United States Patent
Choi et al.

(10) Patent No.: US 11,213,212 B2
(45) Date of Patent: Jan. 4, 2022

(54) APPARATUS FOR MEASURING BLOOD PRESSURE, AND METHOD FOR MEASURING BLOOD PRESSURE BY USING SAME

(71) Applicant: SAMSUNG ELECTRONICS CO., LTD., Suwon-si (KR)

(72) Inventors: Byung-hun Choi, Suwon-si (KR); Hyun-woo Koh, Yongin-si (KR); Hyun-su Kim, Seoul (KR); Hyun-jae Baek, Seoul (KR); Jae-wook Shin, Suwon-si (KR); Chi-yul Yoon, Hwaseong-si (KR); Jae-geol Cho, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 816 days.

(21) Appl. No.: 15/780,827

(22) PCT Filed: Nov. 14, 2016

(86) PCT No.: PCT/KR2016/013057
§ 371 (c)(1),
(2) Date: Jun. 1, 2018

(87) PCT Pub. No.: WO2017/099374
PCT Pub. Date: Jun. 15, 2017

(65) Prior Publication Data
US 2018/0353089 A1    Dec. 13, 2018

(30) Foreign Application Priority Data

Dec. 7, 2015  (KR) .................... 10-2015-0173149
Sep. 20, 2016 (KR) .................... 10-2016-0120252

(51) Int. Cl.
*A61B 5/021* (2006.01)
*A61B 5/00* (2006.01)
(Continued)

(52) U.S. Cl.
CPC ...... *A61B 5/02108* (2013.01); *A61B 5/02007* (2013.01); *A61B 5/02125* (2013.01);
(Continued)

(58) Field of Classification Search
None
See application file for complete search history.

(56) References Cited

U.S. PATENT DOCUMENTS

| 7,674,231 B2 | 3/2010 | McCombie et al. |
| 2008/0214942 A1 | 9/2008 | Oh et al. |

(Continued)

FOREIGN PATENT DOCUMENTS

| JP | 2006-263128 | 10/2006 |
| JP | 2007-313145 | 12/2007 |

(Continued)

OTHER PUBLICATIONS

International Search Report for PCT/KR2016/013057, dated Jan. 10, 2017, 4 pages.
(Continued)

*Primary Examiner* — Michael R Bloch
(74) *Attorney, Agent, or Firm* — Nixon & Vanderhye, P.C.

(57) ABSTRACT

An apparatus for measuring blood pressure, and a method for measuring blood pressure by using the same are disclosed. The disclosed method for measuring blood pressure comprises the steps of: calculating pulse wave transit time; measuring vascular compliance; and measuring systolic blood pressure and diastolic blood pressure by using the pulse wave transit time and the vascular compliance, (Continued)

wherein the vascular compliance can be measured respectively in at least two or more different hand shape poses.

15 Claims, 16 Drawing Sheets

(51) Int. Cl.
   *A61B 5/02*      (2006.01)
   *A61B 5/024*     (2006.01)
   *A61B 5/11*      (2006.01)
   *A61B 5/332*     (2021.01)
   *G16H 50/20*     (2018.01)
   *A61B 5/318*     (2021.01)

(52) U.S. Cl.
   CPC ...... *A61B 5/02416* (2013.01); *A61B 5/02438* (2013.01); *A61B 5/1116* (2013.01); *A61B 5/332* (2021.01); *A61B 5/681* (2013.01); *A61B 5/742* (2013.01); *A61B 5/318* (2021.01); *A61B 5/7405* (2013.01); *G16H 50/20* (2018.01)

(56) References Cited

U.S. PATENT DOCUMENTS

| | | | |
|---|---|---|---|
| 2009/0018422 A1* | 1/2009 | Banet | A61B 5/02125 |
| | | | 600/324 |
| 2010/0049059 A1* | 2/2010 | Ha | A61B 5/721 |
| | | | 600/485 |
| 2010/0113947 A1 | 5/2010 | Kim et al. | |
| 2010/0130876 A1* | 5/2010 | Cho | A61B 5/0285 |
| | | | 600/490 |
| 2010/0210956 A1 | 8/2010 | Im | |
| 2010/0241011 A1 | 9/2010 | McCombie et al. | |
| 2010/0274143 A1 | 10/2010 | Kim et al. | |
| 2011/0009718 A1 | 1/2011 | Gavish | |
| 2013/0296723 A1* | 11/2013 | Cho | A61B 5/02108 |
| | | | 600/501 |
| 2014/0364747 A1 | 12/2014 | Woo et al. | |
| 2015/0157220 A1 | 6/2015 | Fish et al. | |

FOREIGN PATENT DOCUMENTS

| | | |
|---|---|---|
| JP | 2014-239979 | 12/2014 |
| KR | 10-2008-0069859 | 7/2008 |
| KR | 10-2009-0052442 | 5/2009 |
| KR | 10-2010-0116880 | 11/2010 |
| KR | 10-2011-0000287 | 1/2011 |
| KR | 10-1068116 | 9/2011 |
| KR | 10-1288391 | 7/2013 |
| WO | 2012-128407 | 9/2012 |

OTHER PUBLICATIONS

Written Opinion of the ISA for PCT/KR2016/013057 and English-language translation, dated Jan. 10, 2017, 13 pages.
Examination Report dated Jul. 11, 2019 in counterpart European Patent Application No. 16873240.2.
Examination Report dated Dec. 20, 2018 in counterpart European Patent Application No. 16873240.2.
Extended European Search Report dated Jul. 20, 2018 in counterpart European Patent Application No. 16873240.
Communication which replaces the previous search report of Jul. 20, 2018 dated Nov. 22, 2018 in counterpart European Patent Application No. 16873240.
Thomas, Simi Susan et al. "Bio Watch: A Noninvasive Wrist-Based Blood Pressure Monitor That Incorporates Training Techniques for Posture and Subject Variability," IEEE Journal of Biomedical and Health Informatics, vol. 20, No. 5, Sep. 2016, pp. 1291-1300.
Baktash, Seddigheh, "Ratio-Independent Arterial Stiffness-Based Blood Pressure Estimation", UO Research—University of Ottawa, Jan. 1, 2014, pp. i-xiv, -84, XP055489112, DOI: 10.20381/ruor-5024.

* cited by examiner

APPARATUS FOR MEASURING BLOOD PRESSURE, AND METHOD FOR MEASURING BLOOD PRESSURE BY USING SAME

This application is the U.S. national phase of International Application No. PCT/KR2016/013057 filed 14 Nov. 2016, which designated the U.S. and claims priority to KR Patent Application No. 10-2015-0173149 filed 7 Dec. 2015, and KR Patent Application No. 10-2016-0120252 filed 20 Sep. 2016, the entire contents of each of which are hereby incorporated by reference.

BACKGROUND

Field

Apparatuses and methods consistent with the present disclosure relate to an apparatus for measuring blood pressure and a method of measuring blood pressure using the same, and more particularly, to an apparatus for measuring blood pressure and a method of measuring blood pressure using the same for detecting, from the wrist, a periodic change occurring when blood flows in a blood vessel via cardiac impulse to measure blood pressure of radial artery.

Description of Related Art

In general, a non-invasive method that does not damage a human body is a method of measuring blood pressure in a hospital and a home. The non-invasive method is broadly classified into a Korotkoff-sound method and an oscillometric method.

In the Korotkoff-sound method, blood pressure is measured by listening to sound generated in a blood vessel through a stethoscope while increasing and reducing pressure in a cuff in a state in which the cuff is wound around an upper arm and the stethoscope is positioned adjacent to the blood vessel. Systolic blood pressure corresponds to cuff pressure at a time point when stethoscope sound is begun to be first heard (or a time point when two or more pulses of stethoscope sound are begun to be heard). Diastolic blood pressure corresponds to cuff pressure at a time point when stethoscope sound completely disappears by continuously reducing cuff pressure.

However, in the Korotkoff-sound method, a measurer measures blood pressure via stethoscope sound heard through a stethoscope and, thus, the measurer needs high proficiency to accurately measure blood pressure. In addition, because a sense in terms of a time point when stethoscope sound is heard is difference for each measurer, different blood pressure is disadvantageously measured for each measurer.

The oscillometric method is a method of measuring blood pressure using an automated machine and has been most widely used, recently. In the oscillometric method, a cuff is wound around an upper arm and pressure in the cuff is continuously measured while cuff pressure is increased and, then, is gradually reduced. When the pressure in the cuff is continuously measured, a periodic pressure change of blood in a blood vessel is transmitted to the cuff and, in this case, this pressure change in blood changes cuff pressure. In this case, the systolic blood pressure and the diastolic blood pressure are measured by estimating that cuff pressure at a time point when a cuff pressure change due to a blood pressure change is highest is equal to average blood pressure of a user.

However, in the oscillometric method, high pressure needs to be applied to a cuff and, thus, a blood vessel or textus is damaged due to repeated measurement in the case of a hypertensive patient or the old and the inform with inflexible textus. In addition, currently, numerous devices have been introduced but most devices have a large volume and, thus, a user has a difficulty in measuring blood pressure using such a device while carrying the device.

The above two methods of measuring blood pressure commonly use a cuff. Conversely, there is a method of measuring blood pressure using a light sensor instead of a cuff. In the blood pressure measuring method, a pulse transit time (PTT) is calculated using electrocardiogram and photo-plethysmograph (PPG) measured at a finger and blood pressure is estimated using the calculated value. Here, the PPG indicates a pulsation component that is used as a bio signal obtained by irradiating the human body with light in a specific wavelength band and detecting reflected or transmitted light and is generated due to a cardiac impulse. Bio signal measurement using PPG is a non-restraint and non-invasive method and it is possible to detect a multiple signal such as pulse, respiration, and oxygen saturation using a single sensor. A time interval of detecting a pulse wave of PPG from an electronic signal of electrocardiogram (ECG) is referred to as PTT and has a correlation with blood pressure. As such, the method using the PTT measures blood pressure without using of a separate cuff and simultaneously measures PPG and electrocardiogram and calculates the PTT to estimate blood pressure.

However, the PTT is changed by not only a change in blood pressure but also other causes and, thus, there is a problem in that a high measurement error occurs depending on a state of a measurer compared with the above methods using a cuff.

SUMMARY

The present disclosure provides a blood pressure measuring apparatus that is small sized to be worn on the wrist and measures blood pressure in consideration of both a pulse transit time (PTT) and an arterial stiffness index (ASI) that are calculated through photo-plethysmograph (PPG) and electrocardiogram (ECG) to more accurately measure blood pressure, and a blood pressure measuring method using the blood pressure measuring method.

According to an aspect of the present disclosure, a blood pressure measuring method includes calculating a pulse transit time (PTT), measuring an arterial stiffness index (ASI), and calculating systolic blood pressure and diastolic blood pressure using the PTT and the ASI, wherein the ASI is measured in each of at least two or more postures with different hand shapes.

The hand shapes may be taken by any one of spreading all fingers or folding at least one finger, closing a first or spreading at least one finger while the first is closed, by folding a finger, allowing at least two fingers to contact each other, and spacing all fingers apart from each other. In this case, the hand shape may be taken by bending the wrist in any one direction.

The hand shape may be taken by bending the wrist in any one direction and may be taken by bending the wrist at a predetermined angle.

According to another aspect of the present disclosure, a blood pressure measuring method includes measuring calibration systolic blood pressure and calibration diastolic blood pressure, calculating a pulse transit time (PTT) and an arterial stiffness index (ASI) in a state in which at least two different hand shapes are taken, and calculating the calibration systolic blood pressure and calibration diastolic blood pressure, calibration pulse transit time and calibration ASI, and systolic blood pressure and diastolic blood pressure through the calculated PTT and ASI.

The PTT may be calculated using the PPG signal and the electrocardiogram signal.

The ASI may be calculated according to a following math formula by measuring reference pressure applied to a wrist and fluctuation pressure according to cardiac impulse under the reference pressure with respect to each hand shape and obtaining a graph satisfying values corresponding to the reference pressure and the fluctuation pressure:

$$y = a \cdot e^{bx} + c$$

where x is the reference pressure, y is the fluctuation pressure, b is the ASI, and 'a' and 'c' are constants.

The diastolic blood pressure may be calculated according to following math formulae:

$$P_{SD0} = P_{S0} - P_{D0}$$

where $P_{S0}$ is calibration systolic blood pressure and $P_{D0}$ is calibration diastolic blood pressure.

$$P_{SD} = P_{SD0} \left( \frac{e^b}{e^{b_0}} \right) \left( \frac{PTT_0}{PTT} \right)^2$$

where $PTT_0$ is a calibration pulse transit time, PTT is a pulse transit time during blood pressure measurement, $b_0$ is a calibration ASI, and b is an ASI during blood pressure measurement.

$$P_D = \frac{e^b(b_0 - b)}{0.018} + \frac{e^b}{e^{b_0}}(P_{D0} + k_0 P_{SD0}) - kP_{SD}$$

where $P_D$ is diastolic blood pressure during blood pressure measurement and k is a constant.

The systolic blood pressure may be obtained according to a following math formula:

$$P_S = P_D + P_{SD}$$

where $P_S$ is systolic blood pressure during blood pressure measurement.

The k may be calculated according to a following math formula:

$$k = \frac{\int_a^b f(x)}{|Bb - Ba| \cdot H}$$

where $\int_a^b f(x)$ is an area of a waveform configured by fluctuation pressure, Bb-Ba is a width of a fluctuation waveform, and H is a height of the fluctuation waveform.

The blood pressure measuring method may further include guiding a first hand shape, measuring a first pressure deviation applied to a wrist for a predetermined time, re-guiding the first hand shape when the first pressure deviation is not within a predetermined range and measuring a first ASI when the first pressure deviation is within the predetermined range, guiding a second hand shape, determining whether a first inclination of pressure applied to the wrist is greater than a second inclination of pre-measured pressure applied to the wrist as a hand shape is changed to the second hand shape from the first hand shape, re-guiding the second hand shape when the first inclination is less than the second inclination and measuring a second pressure deviation applied to the wrist for a predetermined time when the first inclination is greater than the second inclination, and re-guiding the second hand shape when the second pressure deviation is not within a predetermined range and measuring a second ASI when the second pressure deviation is within the predetermined range.

The first and second hand shapes may be guided to at least one of an image, a text, and voice.

The measuring of the ASI may include guiding a predetermined wearing posture of a blood pressuring measuring apparatus according to whether an ECG signal is detected.

According to another aspect of the present disclosure, a blood pressure measuring apparatus includes a wearing portion configured to be worn to be wound around a wrist of a user, a sensor disposed on the wearing portion and configured to detect a pulse transit time (PTT) and an arterial stiffness index (ASI) of the user, a controller configured to calculate systolic blood pressure and diastolic blood pressure of the user using the PTT and the ASI detected by the sensor, and a display configured to display the systolic blood pressure and diastolic blood pressure calculated by the controller, wherein the sensor detects pressure in a state in which at least two different hand shapes are taken to vary a degree pressurized to the wrist by the wearing portion.

The sensor may include a PPG sensor, an electrocardiogram sensor, and a pressure sensor.

The sensor may detect reference pressure applied to a wrist of a user and fluctuation pressure varied according to cardiac impulse under the reference pressure as pressure of a cell, which is installed on the wearing posture and into which air is injected, to pressurize the cell according to a hand shape.

The sensor may be disposed on one surface of the wearing portion to directly detect pressure applied to a wrist of a user according to a hand shape.

The sensor may be disposed between the wearing portion and the wrist.

DETAILED DESCRIPTION OF THE EXAMPLE EMBODIMENTS

Figure 1:
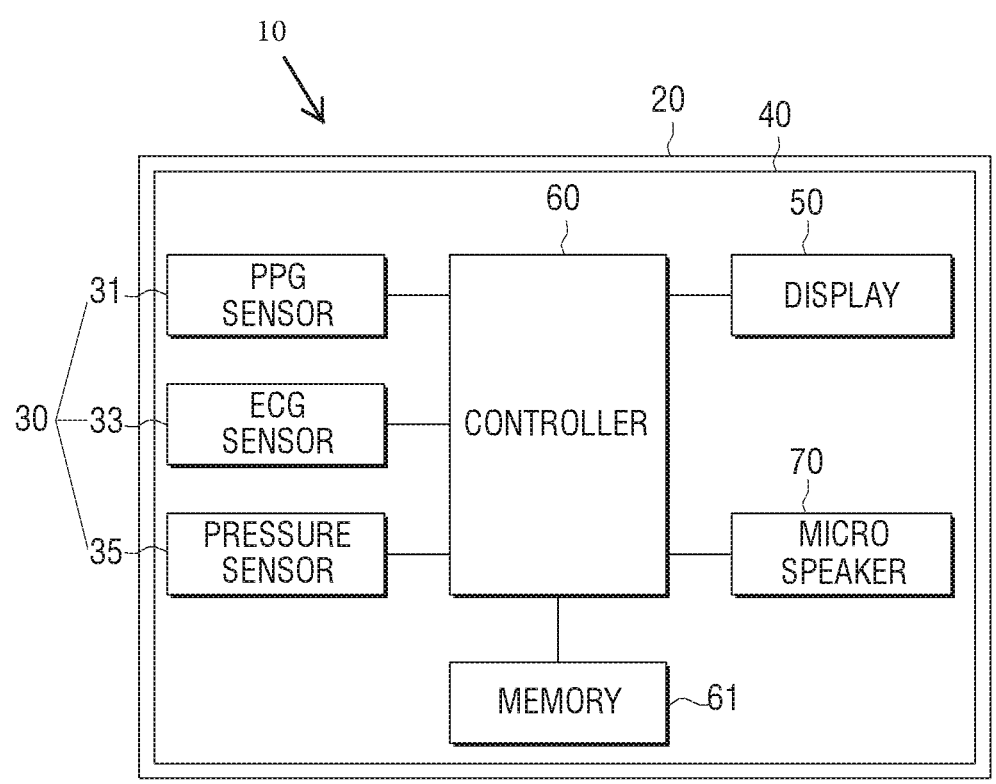
FIG. 1 is a schematic block diagram a blood pressure measuring apparatus according to an exemplary embodiment of the present disclosure.

The present disclosure will now be described more fully with reference to the accompanying drawings, in which exemplary embodiments of the present disclosure are shown. However, this is not intended to limit the present disclosure to particular modes of practice, and it is to be appreciated that all modification, equivalents, and alternatives that do not depart from the spirit and technical scope of the present disclosure are encompassed in the present disclosure. With regard to the description of the drawings, the same reference numerals denote like elements.

The terms, such as "first", "second", and the like used in this disclosure may be used to refer to various elements regardless of the order and/or the priority and to distinguish the relevant elements from other elements, but do not limit the elements. For example, "a first user device" and "a second user device" indicate different user devices regardless of the order or priority. For example, without departing the scope of the present disclosure, a first element may be referred to as a second element, and similarly, a second element may be referred to as a first element.

Terms used in this disclosure are used to describe specified embodiments and are not intended to limit the scope of another embodiment. The terms of a singular form may include plural forms unless otherwise specified. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal unless expressly so defined in various embodiments of this disclosure. In some cases, even if terms are terms which are defined in this disclosure, they may not be interpreted to exclude embodiments of this disclosure.

The term blood pressure stated in this specification refers to a pressure value exerted on a blood vessel wall when blood transmitted from the heart flows in a blood vessel and is classified into arterial pressure, capillary blood pressure, venous pressure, and so on according to a name of the blood vessel. In addition, blood pressure is changed by heart beat. In addition, blood pressure includes systolic blood pressure and diastolic blood pressure. Systolic blood pressure is blood pressure when a ventricle contracts and blood is pushed into artery. Diastolic blood pressure is blood pressure when blood is pressed due to stiffness of an arterial wall even if a ventricle is enlarged and blood is not pushed out.

A sphygmus wave is a wave formed while a pulse is transmitted up to peripheral nerves. The pulse is a phenomenon whereby pressure in a blood flow introduced into an aorta appears in other arteries due to a cardiac impulse. That is, whenever the heart contracts, blood is supplied to a whole body from the hart through an aorta and pressure in the aorta is changed. This change in pressure in the aorta is transmitted to peripheral arterioles of the hand and foot. The sphygmus wave corresponds to this change in pressure represented in the form of a waveform.

The blood pressure apparatus according to the present disclosure may belong to a wearable device that is worn around the wrist and may be capable of be carried by a user to simply measure blood pressure anywhere. In particular, the apparatus may detect a pulse transit time (PTT) and an arterial stiffness index (ASI) and may accurately measure blood pressure using the detected values. In this case, to measure an ASI, different hand shapes may be formed according to various shape gestures and different pressures (default pressure) corresponding to the respective hand shapes may be detected. Under this pressure, pressure (fluctuation pressure) that is continuously changed according to heart beat may be detected. As such, under different default pressures for the respective hand shapes, the ASI may be detected via fluctuation pressure indicated according to a cardiac impulse. As described above, the PTT and the ASI may be calculated to calculate accurate blood pressure using the detected values. A detailed method of calculating blood pressure is described below.

Here, the various hand shapes may be, for example, a hand shape that is changed via an action of spreading out the fingers one by one from a state in which the first is closed or a hand shape taken via an action of changing an angle of bending the wrist from a state in which the first is closed or open. These various hand shapes may be used to apply different default pressures to the radial artery. Any hand shape that is not stated in the present exemplary embodiment may also be applied as long as pressure applied to the radial artery is basically changed. The radial artery may be an artery that is branched from an upper arm artery, is reached up to the palm through an edge portion of a bottom arm, and is positioned between the radius and the skin in the wrist part and may be a portion on which the pulse is mainly felt.

Hereinafter, a configuration of a blood pressure measuring apparatus according to an exemplary embodiment of the present disclosure is described in detail and, then, a method of measuring blood pressure using the blood pressure measuring apparatus is described in detail.

Figure 2A:
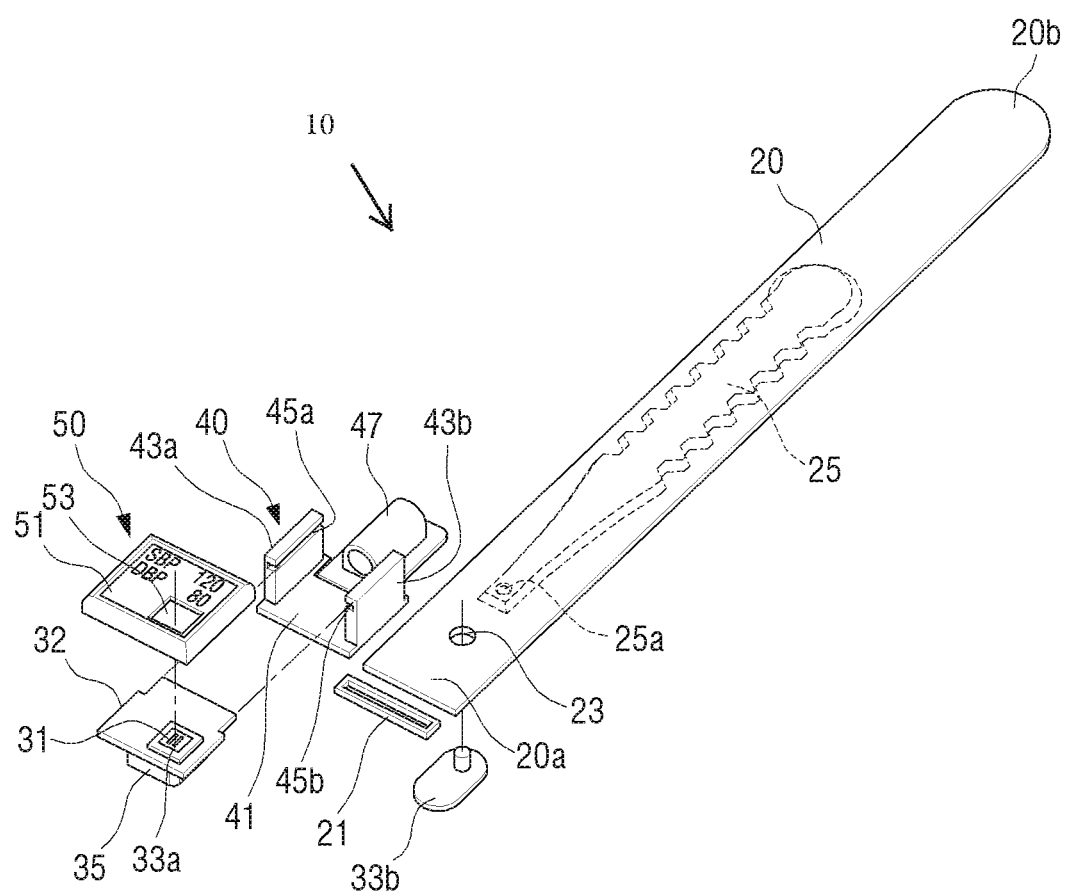
FIG. 2A is an exploded perspective view showing a blood pressure measuring apparatus according to an exemplary embodiment of the present disclosure.
Figure 2B:
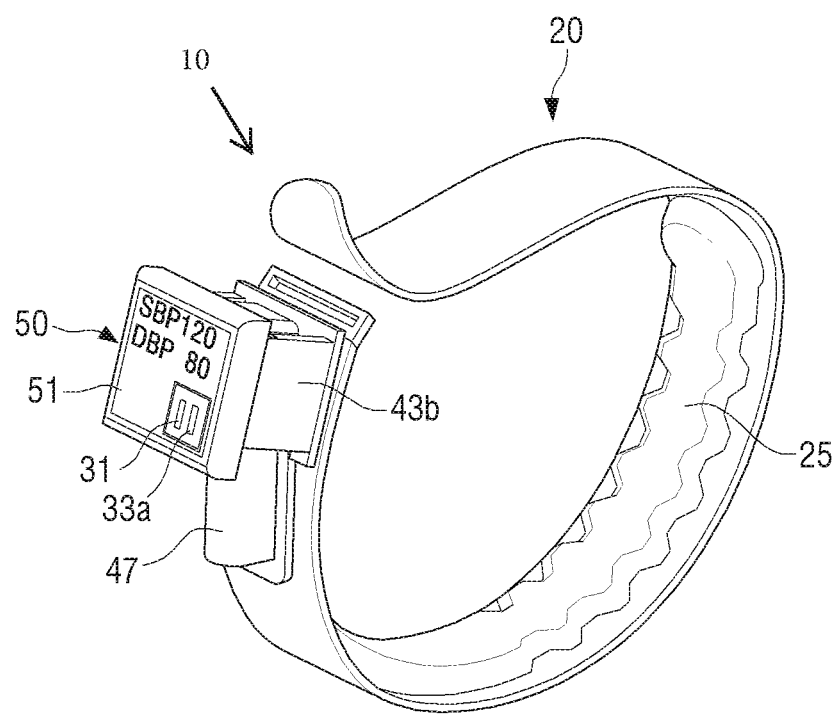
FIG. 2B is a coupling perspective view showing a blood pressure measuring apparatus according to an exemplary embodiment of the present disclosure.

FIG. 1 is a schematic block diagram a blood pressure measuring apparatus according to an exemplary embodiment of the present disclosure. FIGS. 2A and 2B are an exploded perspective view and a coupling perspective view showing a blood pressure measuring apparatus, respectively according to an exemplary embodiment of the present disclosure.

Referring to FIG. 1, a blood pressure measuring apparatus 10 may include a wearing portion 20 worn on the wrist, a sensor 30 for detecting a pressure value and sphygmus wave applied to a blood vessel present in a part at which blood pressure is measured, a support portion 40 coupled to the wearing portion 20 to support the sensor 30, and a display 50 coupled to the support portion 40 to display blood pressure calculated through the pressure value and the sphygmus wave that are detected by the sensor 30. In the specification, to prevent the features of the present exemplary embodiment from being obscure, only hardware components related to the present exemplary embodiment are described. It would be obvious to one of ordinary skill in the art to which the present exemplary embodiment pertains that the blood pressure measuring apparatus includes generic-purpose components other than the hardware components illustrated in FIG. 1.

Referring to FIG. 2A, the wearing portion 20 may have a predetermined length to allow the wearing portion 20 to be worn on the user wrist. When the user takes a predetermined hand shape in a state in which the wearing portion 20 is worn on the user wrist, the radial artery may be pressurized by the wearing portion 20. A one end portion 20a of the wearing portion 20 may include a buckle 21 to maintain the state in which the wearing portion 20 is worn on the wrist. The wearing portion 20 may be worn on the wrist by inserting the other end portion 20b of the wearing portion 20 into the buckle 21 while winding the user wrist. On the other hand, when the other end portion 20b of the wearing portion 20 is separated from the buckle 21, wearing of the wearing portion 20 may be released from the wrist.

A second electrocardiogram electrode 33b that is disposed adjacent to the buckle 21 to detect electrocardiogram may be arranged on the wearing portion 20. The wearing portion 20 may include a through hole 23 to which a portion of the second electrocardiogram electrode 33b is coupled and which is formed in a corresponding portion on which the second electrocardiogram electrode 33b is arranged. The second electrocardiogram electrode 33b may be fixed to the wearing portion 20 as the portion of the second electrocardiogram electrode 33b is coupled to the through hole 23.

A cell 25 into which air is injected may be formed in the wearing portion 20 along a longitudinal length thereof. The cell 25 may contact a portion of the user wrist in a state in which the wearing portion 20 is worn the wrist. When the user changes the hand shape to measure blood pressure, the cell 25 may be pressurized by an external surface of the wrist as the thickness of the wrist is changed. The thickness of the wrist may be changed as the wrist muscle contracts or is relaxed when the user takes a predetermined hand shape. For example, the thickness of the wrist in a state in which all fingers are spread may be larger than that of the wrist in a state in which the first is closed. As the wrist is changed, pressure applied to the cell 25 may also be changed. The changed pressure of the cell 25 may be detected by a pressure sensor 35.

The sensor 30 may detect a pressure value and sphygmus wave applied to the blood vessel. Here, the blood vessel refers to a blood vessel inside a part that is pressurized while pressure is applied to the part as a measurement target part of blood pressure in a state in which the user maintains a predetermined hand shape.

The sensor 30 may include a photo-plethysmograph (PPG) sensor 31 and an electrocardiogram (ECG) sensor 33 for calculation of a pulse transit time (PTT). The sensor 30 may also include the pressure sensor 35 for calculation of pressure of radial artery depending on a hand shape to measure the arterial stiffness index (ASI).

The PPG sensor 31 may be a sensor for analyzing a signal obtained by emitting light beams with two or more different wavelengths to a user finger that contacts a first electrocardiogram electrode 33a of the ECG sensor 33 and receiving the light beams. In this case, the PPG sensor 31 may also be used as an oxygen saturation sensor and, in this regard, the oxygen saturation may be mainly used to calculate calorie consumption according to user activity and may also be used to monitor a situation such as labored respiration, clouded consciousness, shock, body condition during exercise, adult respiratory distress syndrome (ARDS) that is a lung disease, hypoxia risk detection in an alpine region, gas poisoning, and a choking incident. The PPG sensor 31 may be arranged adjacent to the first electrocardiogram electrode 33a of the ECG sensor 33, as shown in FIG. 2A.

The ECG sensor 33 may also be referred to as an electrocardiography (EKG) sensor and may be a sensor for detection of a pattern signal of action current of the heart. The electrocardiogram sensor may be classified into a current electrocardiograph and a voltage electrocardiograph according to a signal detection method. The electrocardiogram waveform may include P, Q, R, S, and T waves. Thereamong, the R wave may correspond to a peak signal and, thus, may be mainly used to analyze a bio signal. For example, a hear rate may be measured through the number of R-wave signals generated per unit time and may be used to diagnose arrhythmia such as tachycardia or bradycardia and to measure overall heart performance ability.

The ECG sensor 33 may include the two electrocardiogram electrodes 33a and 33b to measure electrocardiogram. The first electrocardiogram electrode 33a may be disposed on the other surface of a printed circuit board 32 and may be arranged adjacent to the PPG sensor 31. Accordingly, when a user measures blood pressure, a finger F of the other hand R on which the blood pressure measuring apparatus 10 is not worn may simultaneously contact the first electrocardiogram electrode 33a and the PPG sensor 31 of the ECG sensor 33. The second electrocardiogram electrode 33b may be arranged on one surface of the wearing portion 20 to contact an upper portion of the wrist when the wearing portion 20 is worn on the wrist. In this case, the second electrocardiogram electrode 33b may be maintained to be electrically connected to the ECG sensor 33 installed on the printed circuit board 32. The ECG sensor 33 may detect a pattern signal of action current of the heart using a voltage difference between the first and second electrocardiogram electrodes 33a and 33b.

The pressure sensor 35 may measure default pressure applied to the radial artery by the wearing portion 20 and fluctuation pressure varied according to a cardiac impulse with respect to a predetermined hand shape when the user takes the predetermined hand shape. In this case, the pressure sensor 35 may be connected to the cell 25 formed in the wearing portion 20 through a connection tube 47. Accordingly, the pressure sensor 35 may indirectly detect the default pressure and the fluctuation pressure through pressure of the cell 25 and a change in the pressure.

The support portion 40 may be used as a connection element for coupling the sensor 30 to the wearing portion 20. The support portion 40 may include a coupling piece 41 fixed to one surface of the wearing portion 20, a pair of protrusion pieces 43a and 43b that protrude in parallel to each other to be spaced apart from one surface of the coupling piece 41 at a predetermined interval, and the connection tube 47.

The coupling piece 41 may be fixed to the wearing portion 20 via adhesives or thermosetting or, needless to say, may be fixed to the wearing portion 20 through a general coupling hole such as a screw.

The pair of protrusion pieces 43a and 43b may include slots 45a and 45b formed therein to slidably couple opposite ends of the printed circuit board 32 to the slots 45a and 45b, respectively. In addition, the display 50 may be coupled to upper ends of the pair of protrusion pieces 43a and 43b.

The connection tube 47 may be connected to a connection hole 25a formed in the cell 25 through a predetermined connection pipe (not shown) and, thus, may be indirectly connected to the pressure sensor 35.

The display 50 may include a display region 51 disposed on one surface thereof to display UI/UX. The display region 51 may display the measured systolic blood pressure (SBP) and diastolic blood pressure (DBP) or display a guidance message for blood pressure measurement, that is, a message indicating finger F contact with an electrode, a message indicating that at least two hand shapes need to be maintained for respective predetermined time periods (several seconds), and a message indicating that blood pressure measurement is completed.

When a current posture is not an appropriate posture (hand shape) for blood pressure measurement, the display 50 may display a notice indicating this.

The display 50 may display various pieces of information such as current time when blood pressure is not measured.

The display 50 may include a touchscreen and display UI/UX for input of information as well as information to receive data directly from the user. For example, in some embodiments, when blood pressure is measured, user blood pressure measured by a general blood pressure measurer needs to be input at least one time and, in this case, the display 50 may receive the user blood pressure through the UI/UX displayed on the display region 51.

The display 50 may include an exposure hole 53 that is formed in one side thereof and through which the PPG sensor 31 and the first electrocardiogram electrode 33a of the ECG sensor 33 are exposed. In this case, the exposure hole 53 may be arranged on the same surface as one surface of the display 50, on which the display region 51 is formed.

A controller 60 may receive signals detected from the sensor 30 and calculate blood pressure through the signals. The controller 60 may include a microprocessor installed on the printed circuit board 32. The controller 60 may be electrically connected to a memory 61 that temporarily stores the detected signal and the memory 61 may store a program a program for calculate the detected signal. The program may calculate a PTT using user systolic blood pressure and diastolic blood pressure measured through a separate blood pressure measuring device and a PPG detection value and ECG detection value detected by the sensor 30 and may also be programmed to execute the following math formulae for calculating an arterial stiffness index (ASI) to calculate systolic blood pressure and diastolic blood pressure according to blood pressure measurement of the user.

The controller 60 may control the display 50 to display the user systolic blood pressure and diastolic blood pressure obtained using the above program on the display region 51.

Although, according to the present exemplary embodiment, blood pressure information is displayed through the display 50 included in the blood pressure measuring apparatus 10, the present exemplary embodiment is not limited thereto and, thus, the measured blood pressure information may be transmitted to a separate device, e.g., a mobile device or immobile device including a display and displayed on the display of the corresponding device. In this case, the blood pressure measuring apparatus 10 may transmit the blood pressure information to the corresponding device and the corresponding device may receive the blood pressure information. As such, to transmit and receive the blood pressure information, the blood pressure measuring apparatus 10 and the corresponding device may each include a wireless mobile module (e.g., a wireless mobile module using Bluetooth, Wi-Fi, ZigBee, or the like).

The blood pressure measuring apparatus 10 according to the present exemplary embodiment of the present disclosure may further include a micro speaker 70 for output of guidance voice or guidance sound to allow a user to further move the hand or to take another hand shape when a hand shape taken to measure an ASI does not apply sufficient pressure to a blood vessel. Needless to say, a character or image corresponding to the guidance voice may be displayed through the display 50 of the blood pressure measuring apparatus 10. When the blood pressure measuring apparatus 10 is connected to a mobile device, the guidance voice or the guidance sound may be output through a speaker installed in the mobile device and the character or image corresponding to the guidance voice may be displayed through the display of the mobile device.

The blood pressure measuring apparatus 10 according to the present exemplary embodiment may predetermine time for blood pressure measurement and, when the predetermined time elapses during blood pressure measurement, sound, character, or image information indicating that measurement is completed to the user may be displayed through the display 50 or the micro speaker 70.

Figure 3:
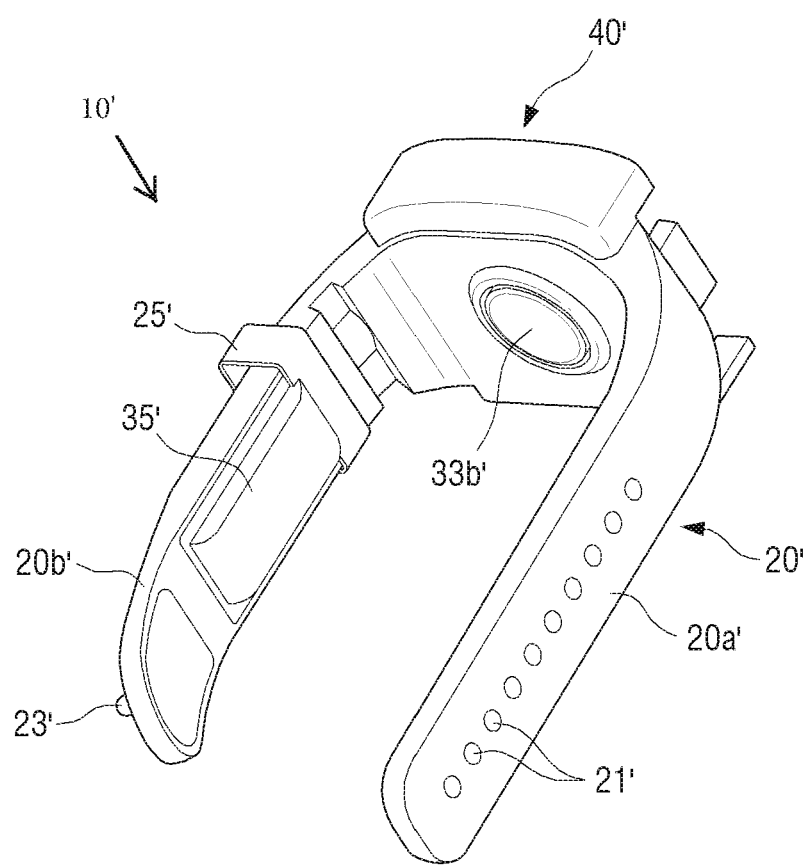
FIG. 3 is a perspective view showing an example in which a position of a pressure sensor is changed.

FIG. 3 is a perspective view showing an example in which a position of a pressure sensor is changed.

Referring to FIG. 3, a blood pressure measuring apparatus 10' may include components, most of which are the same as those of the aforementioned blood pressure measuring apparatus 10. However, a position of a pressure sensor 35' may be set to one surface of a wearing portion 20'. In this case, the pressure sensor 35' may directly contact the wrist when the wearing portion 20' is worn on the wrist and, when the user takes a predetermined hand shape to measure blood pressure, pressure applied to the wrist (i.e., the radial artery of the wrist) may be directly detected without the cell 25. Accordingly, the cell 25 and the connection tube 47 connected to the cell 25 may be omitted.

The pressure sensor 35' may be electrically connected to the controller 60 to transmit the detected pressure signal to the controller 60. A second electrocardiogram electrode 33b' of an ECG sensor may be arranged on one surface of the wearing portion 20', on which the pressure sensor 35' is disposed, to contact an upper portion of the wrist.

In the blood pressure measuring apparatus 10', a configuration of the wearing portion 20' may be slightly different from the aforementioned blood pressure measuring apparatus 10'. That is, the wearing portion 20' may include a plurality of coupling holes 21' that are formed in one side portion 20a' with respect to a portion, to which a support portion 40' is coupled, to be spaced apart from each other at a predetermined interval in a longitudinal direction of the wearing portion 20', and a coupling protrusion 23' formed on the other side portion 20b' to be coupled to any one of the plurality of coupling holes 21'. In this case, a buckle 25' to which the one side portion 20a' is coupled may be arranged on the other side portion 20b' of the wearing portion 20'.

Hereinafter, a procedure of detecting blood pressure using the blood pressure measuring apparatus 10 according to the present disclosure is sequentially described with reference to FIGS. 4 to 10.

Figure 4:
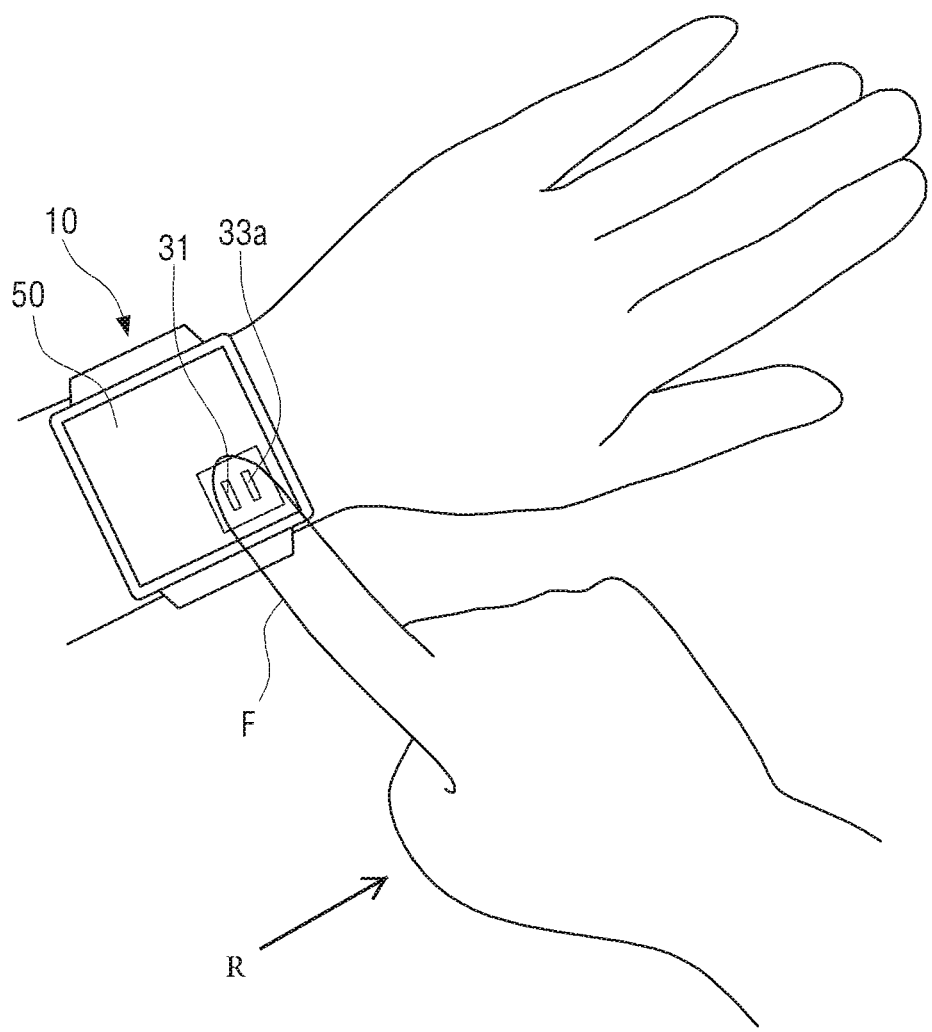
FIG. 4 is a perspective view showing a state in which a blood pressure measuring apparatus is worn on the wrist to measure blood pressure according to an exemplary embodiment of the present disclosure.
Figure 5:
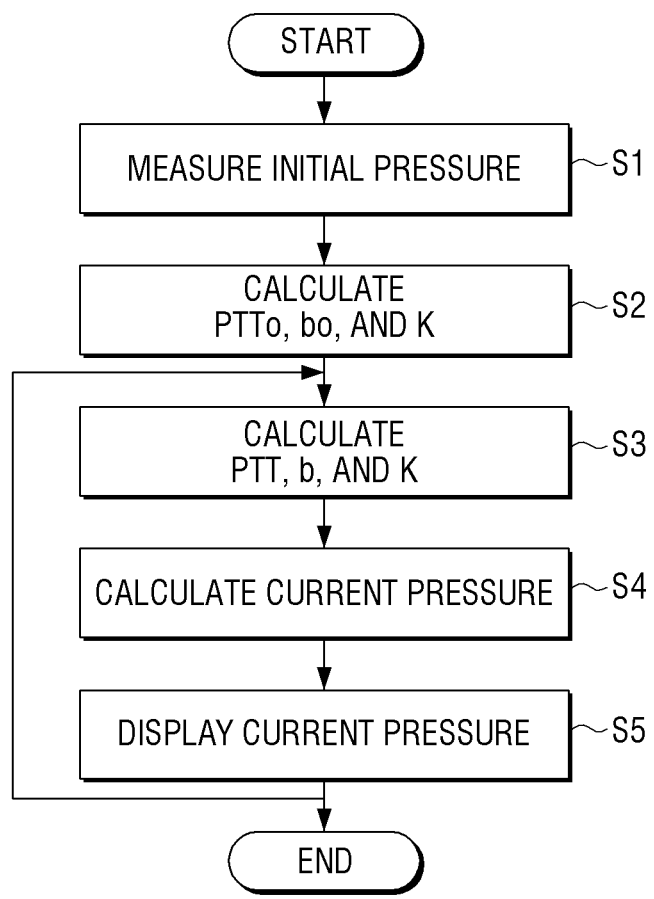
FIG. 5 is a flowchart of a method of measuring blood pressure according to an exemplary embodiment of the present disclosure.

FIG. 4 is a perspective view showing a state in which a blood pressure measuring apparatus is worn on the wrist to measure blood pressure according to an exemplary embodiment of the present disclosure. FIG. 5 is a flowchart of a method of measuring blood pressure according to an exemplary embodiment of the present disclosure.

Referring to FIG. 4, in the blood pressure measuring method according to the present exemplary embodiment, as a first operation, user calibration systolic blood pressure PS0 and calibration diastolic blood pressure PD0 measured through a general blood pressure measurer (S1). As shown in FIG. 5, in a state in which the blood pressure measuring apparatus 10 is worn the wrist, a calibration pulse transit time value $PTT_0$, a calibration ASI value $b_0$, and a calibration k value $k_0$ may be calculated through the blood pressure measuring apparatus 10 (S2).

Then, when blood pressure is measured through the blood pressure measuring apparatus 10 according to the present exemplary embodiment, a pulse transit time value PTT, an ASI value b, and a k value k may be calculated through the blood pressure measuring apparatus 10 without necessity of a separate general blood pressure measurer (S3) and systolic blood pressure PS and diastolic blood pressure PD may be calculated according to Math Formulae 1 to 4 below using the pre-calculated calibration values (the calibration ASI value $b_0$, the calibration pulse transit time value $PTT_0$, and the calibration k value $k_0$) (S4). The calculated systolic blood pressure PS and diastolic blood pressure PD may be displayed on the display region 51 (refer to FIG. 2B) of the display 50.

Operations S1 and S2 are performed only in the first operation in the blood pressure measuring method according to the present exemplary embodiment and only operations S3 to S5 may be performed during next measurement of blood pressure.

In operations S2 and S3, the user may take the following action to detect the pulse transit time values $PTT_0$ and PTT and the ASI values $b_0$ and b.

That is, as shown in FIG. 5, the finger F of a hand that does not wear the blood pressure measuring apparatus 10 may simultaneously contact the PPG sensor 31 and the first electrocardiogram electrode 33a of the ECG sensor 33. In this state, the hand that wears the blood pressure measuring apparatus 10 may be moved to maintain first hand shape for a predetermined time period (several seconds) and, continuously, to maintain second hand shape different from the first hand shape for a predetermined time period (several seconds).

Accordingly, a PPG signal (waveform) and an ECG signal (waveform) may be obtained through the PPG sensor 31 and the ECG sensor 33, respectively, in a state in which the first hand shape and the second hand shape are taken. In this case, a waveform corresponding to the PPG waveform may be calculated using the pressure sensor 35 instead of the PPG sensor 31. According to the present exemplary embodiment, default pressure applied to the radial artery and fluctuation pressure varied according to a cardiac impulse may be calculated through the pressure sensor 35 in a state of the first hand shape and the second hand shape. As such, the PPG signal (waveform), the ECG signal (waveform), the default pressure, and the fluctuation pressure may be detected in a state in which at least two different hand shapes are taken, thereby enhancing the reliability of measurement result.

A PTT value may be calculated through the detected PPG signal (waveform) and ECG signal (waveform) and the ASI may be calculated using the default pressure and the fluctuation pressure. In addition, according to the present exemplary embodiment, the prepared calibration systolic blood pressure $P_{SO}$ and diastolic blood pressure $P_{DO}$, the calibration pulse transit time value $PTT_0$, the calibration ASI value $b_0$, and the calibration k value $k_0$ with the currently measured pulse transit time value PTT, ASI value b, and k value k may be inserted into Math Formulae 1 to 4 below to accurately measure the currently measured blood pressure.

$$P_{SD0} = P_{S0} - P_{D0} \qquad \text{Math Formula 1}$$

$$P_{SD} = P_{SD0}\left(\frac{e^b}{e^{b_0}}\right)\left(\frac{PTT_0}{PTT}\right)^2 \qquad \text{Math Formula 2}$$

$$P_D = \frac{e^b(b_0 - b)}{0.018} + \frac{e^b}{e^{b_0}}(P_{D0} + k_0 P_{SD0}) - k P_{SD} \qquad \text{Math Formula 3}$$

$$P_S = P_D + P_{SD} \qquad \text{Math Formula 4}$$

Hereinafter, a procedure of calculating $PTT_0$ and PTT values, ASI values $b_0$ and b, $k_0$ and k values that are to be inserted into Math Formulae 2 and 3 above through the sensor 30 is described. The values $PTT_0$ and PTT may be calculated using the same procedure, the values $b_0$ and b may be calculated using the same procedure, and the values $k_0$ and k may be calculated using the same procedure and, thus, hereinafter, only a procedure of calculating the values PTT, b, and k is described.

Figure 6:
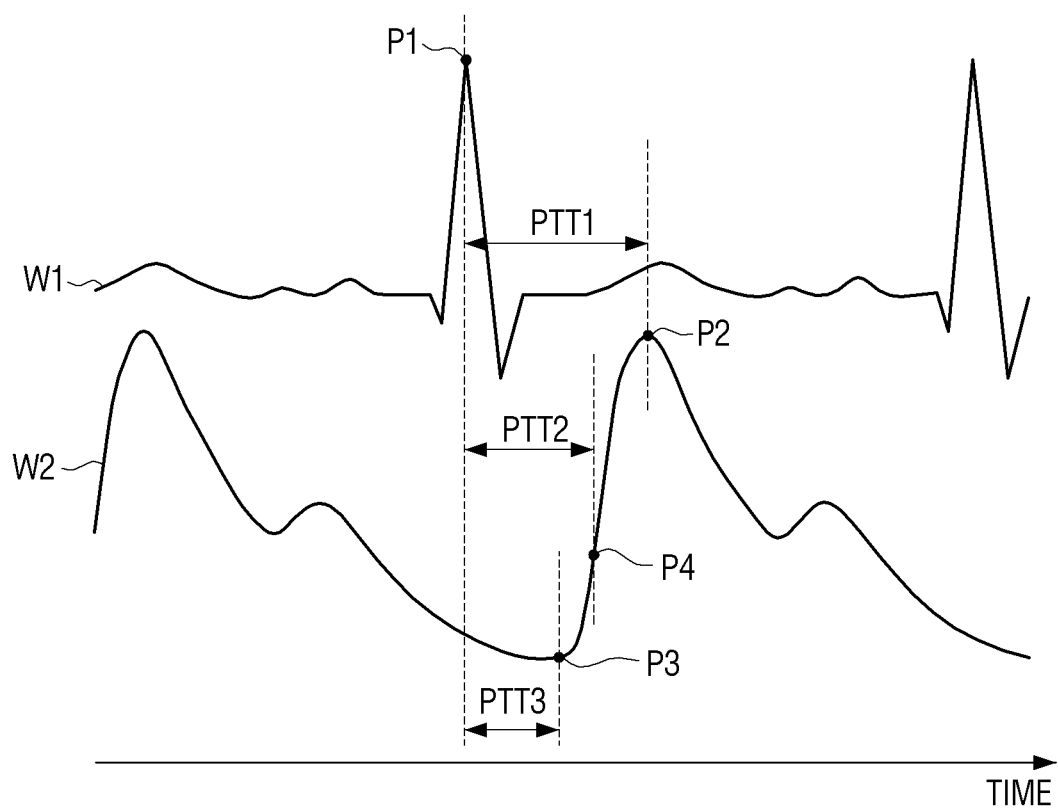
FIG. 6 is a graph showing an output waveform of photoplethysmograph (PPG) and electrocardiogram (ECG).

First, a procedure of calculating a value PTT is described with reference to FIG. 6. FIG. 6 is a graph showing an output waveform of photo-plethysmograph (PPG) and electrocardiogram (ECG).

When being discharged from a left ventricle according to a cardiac impulse, a blood flow may be moved along a blood vessel and a periodic flow thereof may also be detected in the radial artery of the wrist. In this case, an output signal measured every heartbeat through the PPG sensor 31 and the ECG sensor 33 may be indicated by a first waveform W1 and a second waveform W2 shown in FIG. 6. The first waveform may be an output signal detected by the PPG sensor 31 and the second waveform may be an output signal detected by the ECG sensor 33.

In this case, PTT1 indicates an interval between a peak P1 of the first waveform W1 detected by the ECG sensor 33 and a peak P2 of the second waveform W2 detected by the PPG sensor 31, PTT2 indicates an interval between the peak P1 of the first waveform W1 and a valley P3 of the second waveform W2, and PTT3 indicates an interval between the peak P1 of the first waveform W1 and a first differentiation maximum value P4 of the second waveform W2. The value PTT to be applied to the Math Formulae 2 and 3 above may use PTT3 between PTT1 and PTT2.

Then, a procedure of calculating a value b that is an ASI is described with reference to FIG. 7A to 9.

Figure 7A:
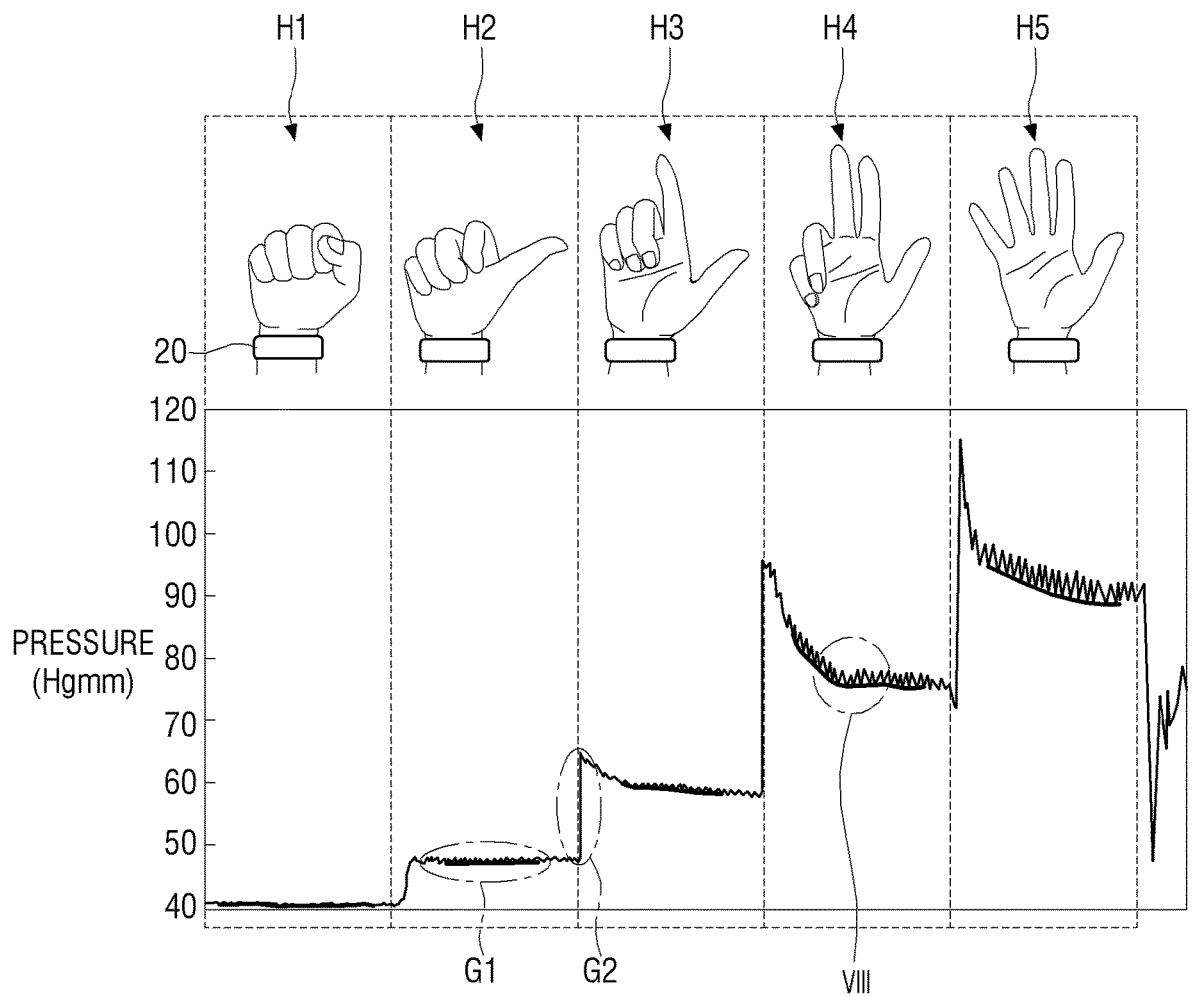
FIG. 7A is a graph showing pressure with respect to different hand shapes for detection of an arterial stiffness index (ASI).
Figure 7B:
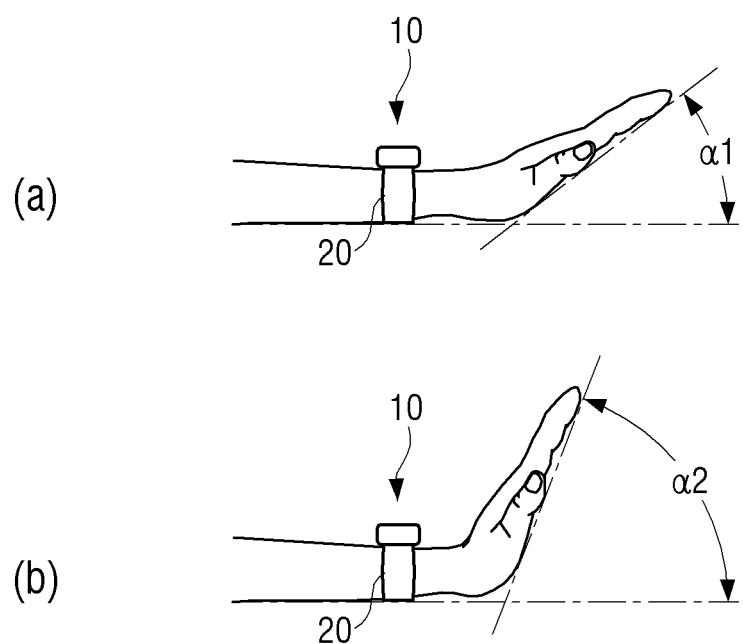
FIG. 7B is a schematic diagram showing a hand shape with a varied angle of bending the wrist.
Figure 8:
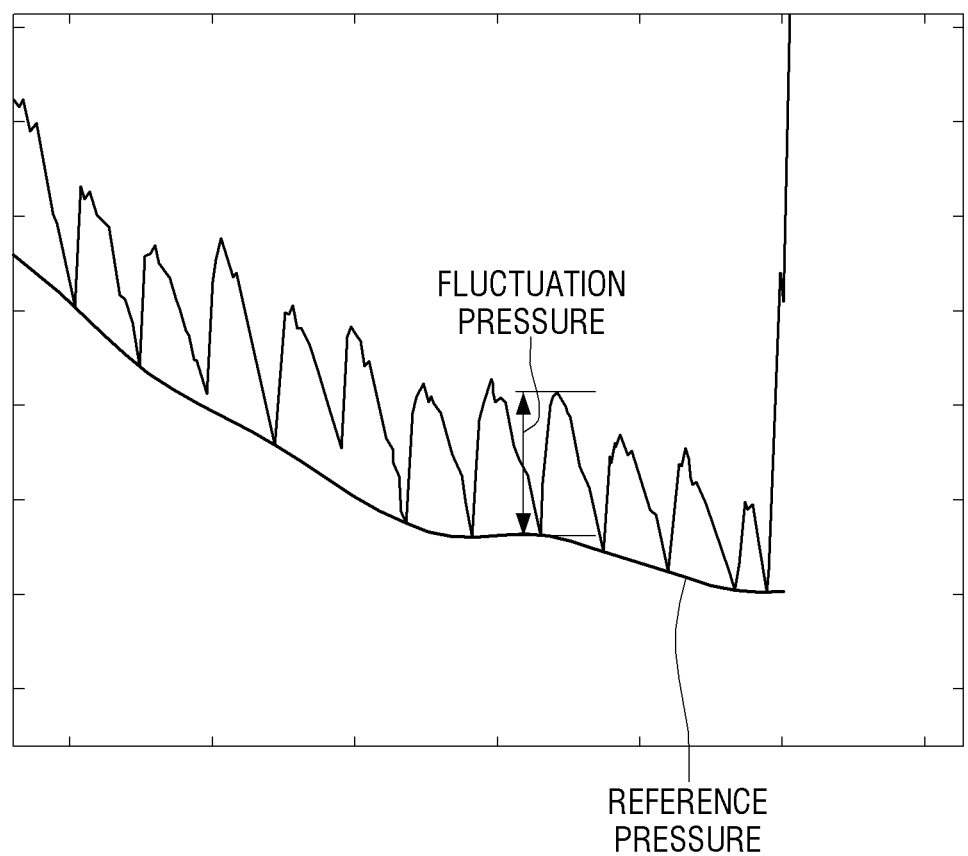
FIG. 8 is an enlarged vie of a portion indicated in FIG. 7A.
Figure 9:
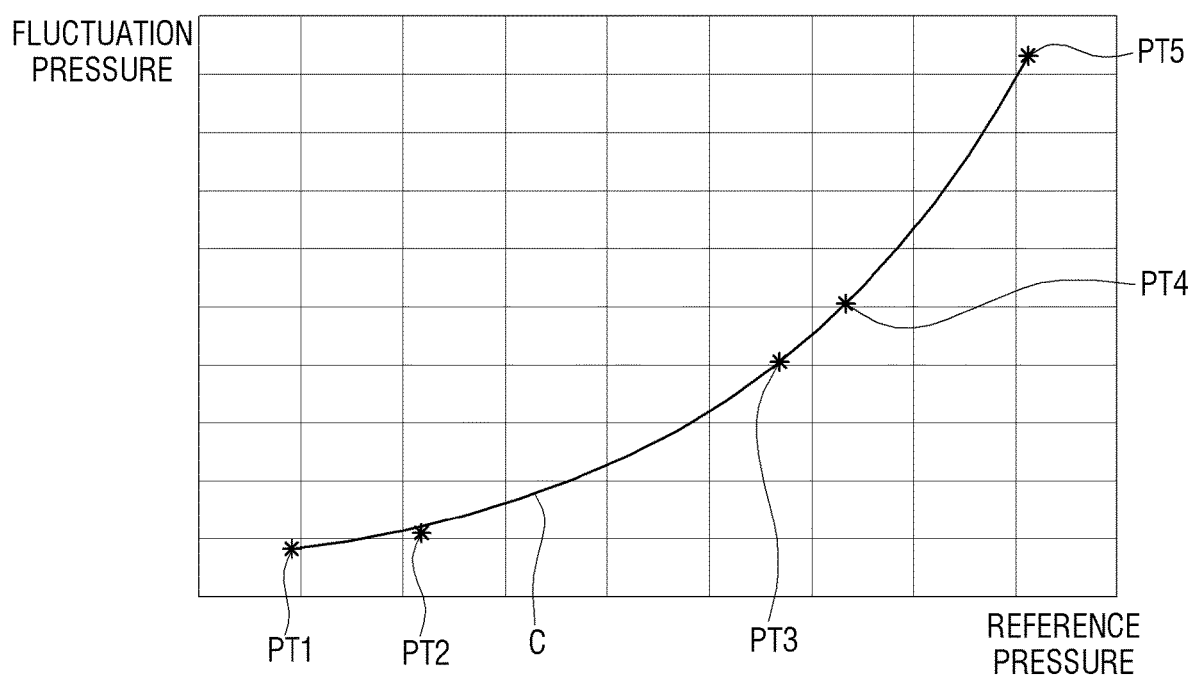
FIG. 9 is a graph showing an ASI obtained via reference pressure and fluctuation pressure corresponding to at least two different hand shapes.

FIG. 7A is a graph showing pressure with respect to different hand shapes for detection of an ASI. FIG. 7B is a schematic diagram showing a hand shape with a varied angle of bending the wrist. FIG. 8 is an enlarged vie of a portion indicated in FIG. 7A. FIG. 9 is a graph showing an ASI obtained via reference pressure and fluctuation pressure corresponding to at least two different hand shapes.

As shown in FIG. 5, when any one of hand shapes is taken by moving fingers in a state in which the blood pressure measuring apparatus 10 according to the present disclosure is worn, pressure measured at the wrist may be changed compared with the case before the hand shape is taken. As such, with regard to a pressure signal measured through the pressure sensor 35 in a state in which any one hand shape is taken, pressure signals in the case of different hand shapes indicate different waveforms and the waveforms reflect a state of a blood vessel, as shown in FIG. 7A.

As shown in FIG. 7A, different hand shapes H1 to H5 indicate different pressures signals and, in this regard, pressure corresponding to hand shapes H2 to H5 in which fingers are spread one by one is increased compared with pressure of the hand shape in which the first is closed. This is because, when the first is closed, muscles at the lower arm and the wrist contract and pressure applied to the wrist by the wearing portion 20 is reduced and, thus, whenever fingers are spread one by one, the pressure applied to the wrist by the wearing portion 20 is gradually increased as the muscles are gradually relaxed.

As such, the present exemplary embodiment may provide a condition of applying pressure with different degrees to the wrist according to a hand shape to measure an ASI.

A hand shape may take various hand shapes other than the example illustrated in FIG. 7A. For example, as shown in FIG. 7B, a posture with a varied angle α1 and α2 of bending the wrist may be taken. Although FIG. 7B shows a hand shape in which the wrist is bent upward, the present exemplary embodiment is not limited thereto and, thus, hand shapes in which the wrist is bent at a predetermined angle in a downward, left, right, or diagonal direction may be taken. In this case, a hand shape in which the wrist is bent and a hand shape in which the wrist is not bent may be interchangeably taken.

Although not shown in the drawing, the hand shapes shown in FIGS. 7A and 7B may be simultaneously taken. That is, in a state in which any one of the hand shapes shown in FIG. 7A is maintained, a hand shape in which the wrist is bent at any one angle may be taken, as shown in FIG. 7B.

Although not shown in the drawing, the hand shape may be taken as any one of hand shapes in which fingers are widely spread in such a way fingers do not contact each other, a hand shape in which at least one finger is folded at a predetermined angle in a state in which all fingers are spread, a hand shape in which fingers are folded, a hand shape in which at least two fingers contact each other, and a hand shape in which all fingers do not contact. When these hand shapes are taken, the wrist may be simultaneously bent.

As such, according to the present exemplary embodiment, a hand shape to measure an ASI is not particularly limited and, thus, any hand shape to be taken by a user may be possible.

When a portion of a pressure signal with respect to any one hand shape H4 shown in FIG. 7A is enlarged, the pressure signal may include reference pressure and fluctuation pressure indicating a fluctuation waveform with respect to the reference pressure, as shown in FIG. 8. The reference pressure is pressure applied to the wrist by the wearing portion 20 according to a hand shape and the fluctuation pressure is pressure that continuously fluctuates according to cardiac impulse under the reference pressure. Amplitude of the fluctuation pressure may be determined according to the size of the reference pressure, a state (hardness) of a blood vessel, and blood pressure.

Referring to FIG. 9, an inclination of a graph of an exponential function represented by Math Formula 5 according to fluctuation pressure corresponding to reference pressure may be calculated to calculate an ASI According to the present exemplary embodiment, according to the fact indicating that, when an ASI is changed, an inclination of a graph of fluctuation pressure measured using an oscillometric method is changed, the inclination of the graph may be calculated to calculate an ASI via a change in pressure measured when different pressures are applied to the wrist according to a hand shape.

$$y = a \cdot e^{bx} \qquad \text{Math Formula 5}$$

Here, x is a value corresponding to default pressure, y is a value corresponding to fluctuation pressure, and 'a' is a constant.

A plurality of points PT1 to PT5 shown in FIG. 9 may be obtained by default pressure and fluctuation pressure corresponding to the five hand shapes H1 to H5 shown in FIG. 7A and, when the points PT1 to PT5 are connected, an exponential function graph shown in FIG. 9 may be obtained.

According to the present exemplary embodiment, to calculate an ASI, all the five hand shapes are taken and the exponential function graph shown in FIG. 9 is obtained via the default pressure and the elastic pressure obtained under each of the hand shapes but, as seen from the above description, a graph of an ASI is represented as a graph of an exponential function and, thus, to calculate default pressure and fluctuation pressure only for at least two hand shapes, an inclination may be calculated through two points to calculate an ASI. Accordingly, a user may measure blood pressure in a state in which at least two different hand shapes are taken.

Math Formula 5 may be represented as an exponential function including a constant 'c' like in Math Formula 6.

$$y = a \cdot e^{bx} + c \qquad \text{Math Formula 6}$$

Figure 10:
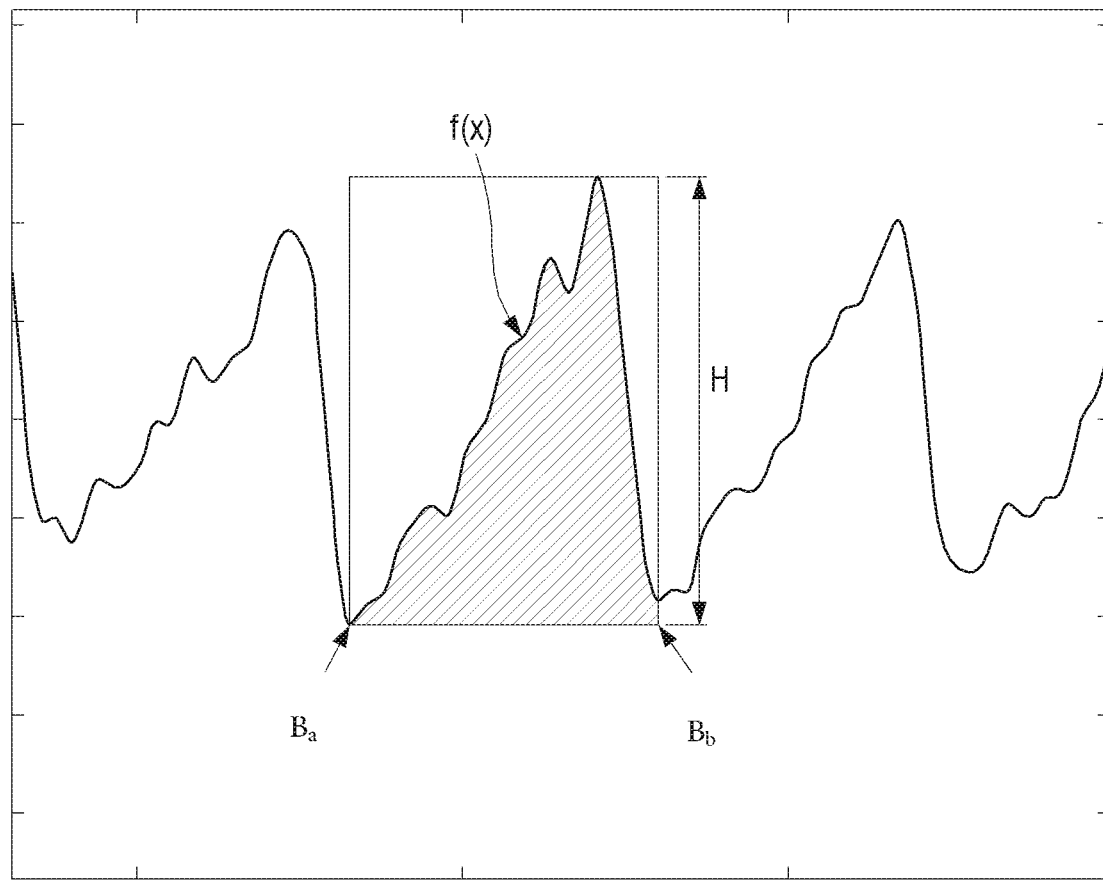
FIG. 10 is a graph showing a ratio of an area occupied by a pressure waveform of a partial period taken from the pressure waveform shown in FIG. 8.

FIG. 10 is a graph showing a ratio of an area occupied by a pressure waveform of a partial period taken from the pressure waveform shown in FIG. 8.

A value k to be applied to Math Formula 3 is a ratio of an area occupied by a fluctuation pressure waveform to an area that is a product of a width Bb-Ba and a height H of the fluctuation pressure waveform as indicated in a math formula 7 below.

$$k = \frac{\int_a^b f(x)}{|Bb - Ba| \cdot H} \qquad \text{Math Formula 7}$$

A value k may be replaced with an appropriate constant to calculate measurement blood pressure rather than being calculated every calibration or measurement time point.

As such, the blood pressure measuring apparatuses 10 and 10' according to the present disclosure may calculate blood pressure in consideration of both the PTT and the ASI to more accurately measure the systolic blood pressure and the diastolic blood pressure.

Table 1 below shows an accuracy difference between the case in which blood pressure is estimated by applying an ASI like in the blood pressure measuring apparatuses 10 and 10' according to the present disclosure and the prior art in which blood pressure is estimated without application of an ASI.

TABLE 1

|  | Prior Art | Present disclosure |
| --- | --- | --- |
| systolic blood pressure | ±9.08 | ±6.38 |
| diastolic blood pressure | ±7.80 | ±6.06 |

Referring to Table. 1 above, an accuracy difference in systolic blood pressure between the present disclosure and the prior art is 2.7 and the accuracy difference in diastolic blood pressure is 1.74. Accordingly, it may be seen that the accuracy according to the present disclosure is enhanced compared with the prior art by about 20% to 30%. As described above, with regard to the blood pressure measuring apparatuses 10 and 10' according to the present disclosure, when the pressure sensor 35' is wound around a portion of the wrist, if the blood pressure measuring apparatus 10' is separated from the wrist and, then, is re-worn on the wrist, a procedure of minutely adjusting a position of the wearing portion 20' to find a position of the radial artery as in the prior art may be omitted. In addition, an arterial stiffness index (ASI) is applied to calculate blood pressure and, thus, a separate structure or user effort for satisfying a similar wearing condition is not required every blood pressure measurement time point, thereby maximizing user convenience.

The blood pressure measuring apparatuses 10 and 10' according to the present disclosure may be small sized to be worn on the wrist like a wrist watch and, thus, it may be advantageous to conveniently managed and stored.

According to the present exemplary embodiment, to measure blood pressure, whether an appropriate hand shape is taken may be determined, and a user may be notified about the determination result to guide the user to take the appropriate hand shape.

Figure 11:
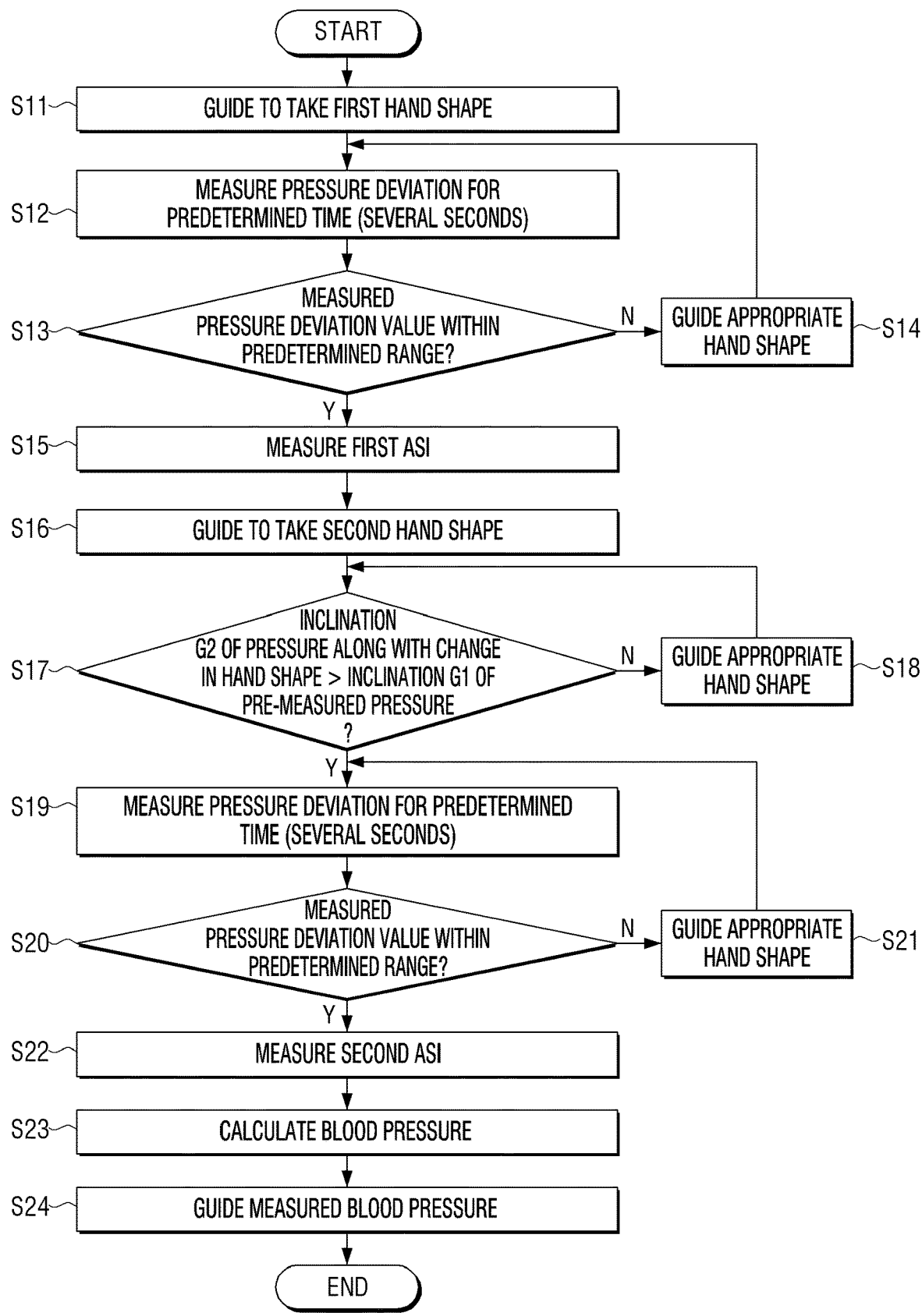
FIG. 11 is a flowchart showing a procedure of measuring blood pressure while guiding a user to take first and second hand shapes.

FIG. 11 is a flowchart showing a procedure of measuring blood pressure while guiding a user to take first and second hand shapes.

Hereinafter, the case in which the first hand shape to be described below is the hand shape H2 of FIG. 7A and the second hand shape is the hand shape H3 of FIG. 7A will be exemplified.

First, when a user begins to measure blood pressure by selecting a menu displayed on the display 50 of the blood pressure measuring apparatus 10 or pressing a predetermined command input button (not shown) included in the blood pressure measuring apparatus 10, an image corresponding to the first hand shape (the hand shape H2 of FIG. 7A) and/or a text for description of the image may be displayed through the display 50 to guide the user to take the corresponding hand shape (S11).

In this case, instead of the guidance through the display 50, guide speech may be output using voice through the micro speaker 70 to guide the first hand shape. In addition, through the display 50 and the micro speaker 70, an image and/or characters may be displayed and, simultaneously, guide speech may be output to guide the first hand shape.

The first hand shape may be guided and a pressure deviation value applied to the wrist for a predetermined time period (several seconds) is measured (S12) and, then, whether the measured pressure deviation value is within a predetermined range may be determined (S13).

When the measured pressure deviation value is not within the predetermined range, an appropriate hand shape with respect to the first hand shape may be guided to the user through the display 50 and/or the micro speaker 70 (S14). Operation S13 may be re-performed.

When the measured pressure deviation value is within the predetermined range, a first ASI may be measured (S15). The first ASI may be measured using the same method as the aforementioned ASI measuring method.

When the first ASI is completely measured, the user may be guided to take the second hand shape (the hand shape H3 of FIG. 7A) through the display 50 and/or the micro speaker 70 (S16).

Then, whether an inclination (i.e., an inclination of pressure applied to the wrist along with a posture change) of a portion G2 of the graph shown in FIG. 7A is greater than an inclination (i.e., an inclination of pressure applied to the wrist prior to a posture change) of a pre-measured portion G1 of the graph shown in FIG. 7A may be determined (S17). In this operation, whether the user changes a hand shape to the second hand shape from the first hand shape may be determined.

When the inclination of the portion G2 is less than the inclination of the pre-measured G1, the hand shape may not be determined to be appropriately changed to the second hand shape from the first hand shape and an appropriate hand shape with respect to the second hand shape may be guided to the user through the display 50 and/or the micro speaker 70 (S18). Operation S17 may be re-performed.

When the inclination of the portion G2 is greater than the inclination of the pre-measured G1, the hand shape may be determined to be appropriately changed to the second hand shape from the first hand shape and a pressure deviation value applied to the wrist for a predetermined time period (several seconds) (S19) and, then, whether the measured pressure deviation value is within the predetermined range may be determined (S20).

When the measured pressure deviation value is not within the predetermined range, an appropriate hand shape with respect to the second hand shape may be guided to the user through the display 50 and/or the micro speaker 70 (S21). Operation S19 may be re-performed.

When the measured pressure deviation value is within the predetermined range, a second ASI may be measured (S22). The second ASI may also be measured using the same method as the aforementioned ASI measuring method.

As such, when the first and second ASIs are measured, blood pressure may be calculated using the aforementioned method (S23) and the measured blood pressure may be guided to the user through the display 50 and/or the micro speaker 70 (S24).

As such, according to the present exemplary embodiment, to measure blood pressure, the user may be easily guided to take at least two different hand shapes, thereby more accurately measuring blood pressure.

Figure 12:
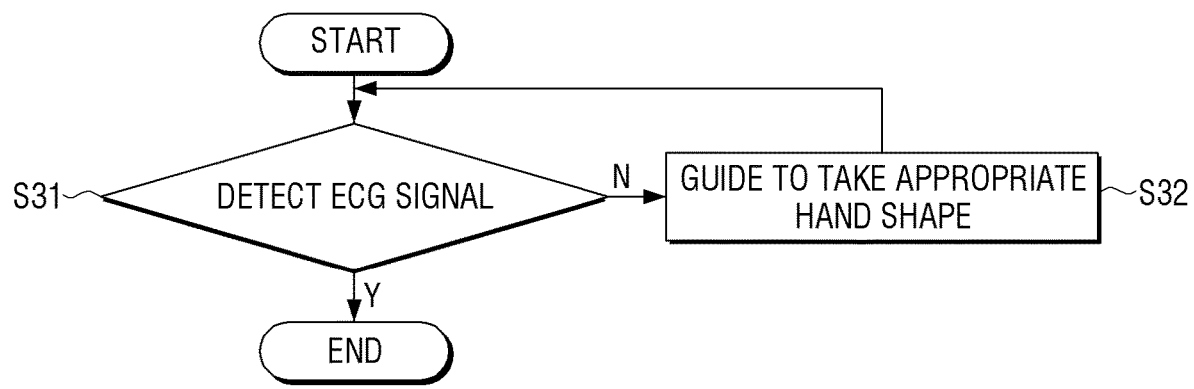
FIG. 12 is a flowchart showing a procedure of determining whether a wearing portion is appropriately worn on the wrist through an ECG signal.
Figure 13A:
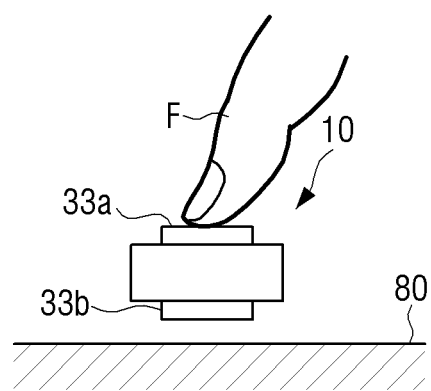
FIG. 13A is a diagram showing a state in which a second electrocardiogram electrode of an ECG sensor is spaced apart from the wrist and FIG. 13B is a diagram showing a state in which a second electrocardiogram electrode of an ECG sensor contacts the wrist.
Figure 13B:
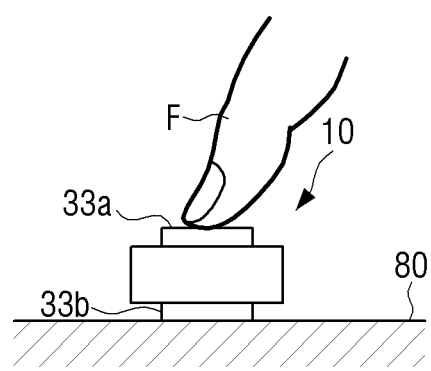

FIG. 12 is a flowchart showing a procedure of determining whether a wearing portion is appropriately worn on the wrist through an ECG signal. FIG. 13A is a diagram showing a state in which a second electrocardiogram electrode of an ECG sensor is spaced apart from the wrist. FIG. 13B is a diagram showing a state in which a second electrocardiogram electrode of an ECG sensor contacts the wrist.

When the blood pressure measuring apparatus 10 is worn on the wrist 80, if a wearing posture is not appropriate, a finger F contacts the first electrocardiogram electrode 33*a* of the ECG sensor 33 as shown in FIG. 13A, but the second electrocardiogram electrode 33*b* may be spaced apart from the wrist (in detail, an upper portion of the wrist) by a predetermined interval.

Under an appropriate wearing posture of the blood pressure measuring apparatus 10 for blood pressure measurement, the finger F may contact the first electrocardiogram electrode 33*a* of the ECG sensor 33 and the second electrocardiogram electrode 33*b* may contact the wrist (in detail, an upper portion of the wrist), as shown in FIG. 13B.

As such, when the second electrocardiogram electrode 33*b* of the ECG sensor 33 is spaced apart from the wrist, it may be difficult to accurately measure blood pressure and, thus, according to the present exemplary embodiment, a signal of the ECG sensor 33 may be detected to guide an appropriate wearing posture of the blood pressure measuring apparatus 10 to the user, as shown in FIG. 12. That is, during blood pressure measurement, whether the ECG signal is detected may be determined through the ECG sensor 33 (S31).

When the ECG signal is not detected, an appropriate wearing posture of the blood pressure measuring apparatus 10 may be guided to the user through the display 50 and/or the micro speaker 70 (S32). Operation S31 may be re-performed. When the ECG signal is detected, it may be determined that the blood pressure measuring apparatus 10 is appropriately worn and, continuously, blood pressure may be measured.

The foregoing exemplary embodiments and advantages are merely exemplary and are not to be construed as limiting the present disclosure. The present teaching can be readily applied to other types of apparatuses. Also, the description of the exemplary embodiments of the present disclosure is intended to be illustrative, and not to limit the scope of the claims, and many alternatives, modifications, and variations will be apparent to those skilled in the art.

INDUSTRIAL APPLICABILITY

The present disclosure relates to a blood pressure measuring apparatus and a blood pressure measuring method using the same.

What is claimed is:

1. A blood pressure measuring method using a wrist-wearable apparatus including a photo-plethysmograph (PPG) sensor, an electrocardiogram (ECG) sensor, and a pressure sensor, the method comprising:
   obtaining a first waveform using the PPG sensor and a second waveform using the ECG sensor;
   obtaining a pulse transit time (PTT) based on the first waveform and the second waveform;
   obtaining an arterial stiffness index (ASI) based on a pressure difference between a first pressure detected at a wrist of a user using the pressure sensor when a hand of the user wearing the apparatus is in a first hand shape and a second pressure detected at the wrist of the user using the pressure sensor when the hand of the user is in a second hand shape different from the first hand shape;
   obtaining systolic blood pressure of the user and diastolic blood pressure of the user using the obtained PTT and the obtained ASI; and
   outputting the obtained systolic blood pressure and diastolic blood pressure.

2. The blood pressure measuring method as claimed in claim 1, wherein the first and second hand shapes comprise hand shapes from a hand shape group including hand shapes in which all fingers of the hand of the user are spread and hand shapes in which at least one finger of the hand of the user is folded.

3. The blood pressure measuring method as claimed in claim 1, wherein the first and second hand shapes comprise hand shapes from a hand shape group including a closed first shape and hand shapes in which at least one finger of the hand of the user is spread while the first is closed.

4. The blood pressure measuring method as claimed in claim 1, wherein the first or second hand shapes comprise hand shapes from a hand shape group including hand shapes in which a finger of the hand of the user is folded.

5. The blood pressure measuring method as claimed in claim 1, wherein the first and second hand shapes comprise hand shapes from a hand shape group including hand shapes in which at least two fingers of the hand of the user contact each other.

6. The blood pressure measuring method as claimed in claim 1, wherein the first or second hand shapes comprise hand shapes from a hand shape group including hand shapes in which all fingers of the hand of the user are spaced apart from each other.

7. The blood pressure measuring method as claimed in claim 1, wherein the first and second hand shapes comprises hand shapes from a hand shape group in which the wrist of the user is bent in any one of different directions.

8. The blood pressure measuring method as claimed in claim 7, wherein the first and second hand shapes comprise hand shapes from a hand shape group in which the wrist of the user is bent at any one of a plurality of different predetermined angles.

9. The blood pressure measuring method as claimed in claim 1, wherein the first or second hand shapes comprise hand shapes from a hand shape group in which the wrist of the user is bent in any one direction.

10. The blood pressure measuring method as claimed in claim 1, wherein the pressure sensor obtains a reference pressure at the wrist of the user and fluctuation pressure according to cardiac impulse under the reference pressure with respect to each of the first and second hand shapes and the ASI is obtained using a graph satisfying values corresponding to the reference pressure and the fluctuation pressure according to a formula:

$$y = a \cdot e^{bx} + c$$

where x is the reference pressure, y is the fluctuation pressure, b is the ASI, and 'a' and 'c' are constants.

11. The blood pressure measuring method as claimed in claim 10, wherein the diastolic blood pressure is calculated according to formulae comprising:

$$P_{SD0} = P_{S0} - P_{D0}$$

where $P_{S0}$ is a calibration systolic blood pressure and $P_{D0}$ is a calibration diastolic blood pressure;

$$P_{SD} = P_{SD0}\left(\frac{e^b}{e^{b_0}}\right)\left(\frac{PTT_0}{PTT}\right)^2$$

where $PTT_0$ is a calibration pulse transit time, PTT is the obtained pulse transit time, $b_0$ is a calibration ASI, and b is the obtained ASI; and $$P_D = \frac{e^b(b_0 - b)}{0.018} + \frac{e^b}{e^{b_0}}(P_{D0} + k_0 P_{SD0}) - k P_{SD}$$

where $P_D$ is the obtained diastolic blood pressure and k is a constant.

12. The blood pressure measuring method as claimed in claim 11, wherein the systolic blood pressure is obtained according to a formula:

$$P_S = P_D - P_{SD}$$

where $P_S$ is the obtained systolic blood pressure.

13. The blood pressure measuring method as claimed in claim 12, wherein the k is calculated according to a formula:

$$k = \frac{\int_a^b f(x)}{|Bb - Ba| \cdot H}$$

where ∫f(x) is an area of a waveform configured by fluctuation pressure, Bb-Ba is a width of a fluctuation waveform, and H is a height of the fluctuation waveform.

14. The blood pressure measuring method as claimed in claim 1, further comprising:
   providing guidance for guiding the hand of the user into the first hand shape;
   obtaining, for a predetermined time while the hand of the user is configured in the first hand shape, a first pressure deviation applied to the wrist of the user;
   based on the first pressure deviation not being within a predetermined range, providing further guidance for configuring the hand of the user into the first hand shape;
   based on the first pressure deviation being within the predetermined range, obtaining a first ASI;
   providing guidance for guiding the hand of the user into the second hand shape;
   determining whether a first inclination of pressure applied to the wrist of the user is greater than a second inclination of pre-measured pressure applied to the wrist of the user as a hand shape of the hand of the user is changed to the second hand shape from the first hand shape;
   based on the first inclination being less than the second inclination, providing further guidance for guiding the hand of the user into the second hand shape when the first inclination is less than the second inclination;
   based on the first inclination being greater than the second inclination, obtaining a second pressure deviation applied to the wrist of the user for a predetermined time;
   based on the second pressure deviation not being within a second predetermined range, providing further guidance for guiding the hand of the user into the second hand shape; and
   based on the second pressure deviation being within the second predetermined range, obtaining a second ASI.

15. A blood pressure measuring apparatus comprising:
   a photo-plethysmograph (PPG) sensor;
   an electrocardiogram (ECG) sensor;
   a pressure sensor;
   a wearing portion configured for wearing around a wrist of a user, the PPG sensor, the ECG sensor and the pressure sensor being disposed in the wearing portion;
   a display; and
   a processor configured to:
      obtain a first waveform using the PPG sensor;
      obtain a second waveform using the ECG sensor;
      obtain a pulse transit time (PTT) based on the first waveform and the second waveform;
      obtain an arterial stiffness index (ASI) based on a pressure difference between a first pressure using the pressure sensor when a hand of a user is in a first hand shape and a second pressure using the pressure sensor when the hand of the user is in a second hand shape different from the first hand shape;
      obtain systolic blood pressure and diastolic blood pressure of the user using the obtained PTT and the obtained ASI; and
      control the display to display the systolic blood pressure and diastolic blood pressure,
   wherein the first and second hand shapes provide different pressures to the wrist of the user by the wearing portion.

* * * * *